US00PP23480P2

(12) United States Plant Patent
Striem et al.

(10) Patent No.: US PP23,480 P2
(45) Date of Patent: Mar. 19, 2013

(54) GRAPEVINE PLANT NAMED 'SUGRAFORTYONE'

(50) Latin Name: *Vitis vinifera*
Varietal Denomination: Sugrafortyone

(75) Inventors: Michael J. Striem, Rehovot (IL); Terry A. Bacon, Bakersfield, CA (US)

(73) Assignee: Sun World International, LLC, Bakersfield, CA (US)

( * ) Notice: Subject to any disclaimer, the term of this patent is extended or adjusted under 35 U.S.C. 154(b) by 0 days.

(21) Appl. No.: 13/374,737

(22) Filed: Jan. 10, 2012

(51) Int. Cl.
*A01H 5/00* (2006.01)

(52) U.S. Cl. ..... Plt./207
(58) Field of Classification Search ..... Plt./207
See application file for complete search history.

*Primary Examiner* — Annette Para
(74) *Attorney, Agent, or Firm* — Knobbe, Martens, Olson & Bear, LLP

(57) ABSTRACT

A new and distinct grapevine variety characterized in that it produces a medium sized, green, near-round berry that ripens very early in the season and has a rudimentary seed trace. The berries of 'Sugrafortyone' are firm, slightly juicy, have medium sugar content and a Muscat flavor. Ripening of the new variety takes place about 5 weeks earlier than the comparable variety 'Sugraeighteen' (U.S. Plant Pat. No. 11,820), and the new variety has near-round berry shape compared to oval shape for the comparable variety 'Sugraone' (U.S. Plant Pat. No. 3,106).

1 Drawing Sheet

Latin name of the genus and species claimed: *Vitis vinifera*. Variety denomination: 'SUGRAFORTYONE'.

BACKGROUND AND SUMMARY OF THE INVENTION

This invention relates to the discovery and asexual propagation of a new and distinct variety of grapevine, 'Sugrafortyone', as herein described and illustrated. The new variety was first hybridized by Michael J. Striem and evaluated by Terry A. Bacon in Wasco, Kern County, Calif. The variety was originated by controlled hybridization.

The new variety 'Sugrafortyone' is characterized by the production of a medium sized, green, near-round berry that ripens very early in the season and has a rudimentary seed trace. The berries of 'Sugrafortyone' are firm, slightly juicy, have a medium sugar content and a Muscat flavor.

The seed parent is the varietal selection '97035-209-287' (unpatented) and the pollen parent is the varietal selection '97029-206-141' (unpatented). The parent varieties were first crossed in May 2002 by Michael J. Striem. The date of first sowing was March 2003, and the date of first flowering was May 2005.

The new variety 'Sugrafortyone' was first asexually propagated in December 2007 in Wasco, Kern County, Calif., by Michael J. Striem using hardwood cuttings.

The new variety 'Sugrafortyone' resembles its seed parent '97035-209-287' (unpatented) in that both have green berries that ripen early in the season. The new variety 'Sugrafortyone' differs from its seed parent in that the new variety ripens earlier in the season, starting about July 3, and has rudimentary seed trace, while the seed parent ripens mid-season, starting about July 25, and has a noticeable seed trace.

The new variety 'Sugrafortyone' differs from its pollen parent '97029-206-141' (unpatented) in that the new variety has green berries and ripens early, starting about July 3, while the pollen parent has red berries and ripens late in the season, starting about September 1.

The new variety 'Sugrafortyone' resembles 'Sugraone' (U.S. Plant Pat. No. 3,106) in having green berries that ripen early in the season. The new variety 'Sugrafortyone' differs from 'Sugraone' in that the new variety has a near-round berry shape compared to an oval berry shape for 'Sugraone'. The new variety 'Sugrafortyone' also resembles 'Sugraeighteen' (U.S. Plant Pat. No. 11,820) in having round green berries and a Muscat aroma. The new variety 'Sugrafortyone' differs from 'Sugraeighteen' in that the new variety ripens about 5 weeks earlier.

The new 'Sugrafortyone' variety has been shown to maintain its distinguishing characteristics through successive asexual propagations by, for example, cuttings.

Variations of the usual magnitude from the characteristics described herein may occur with changes in any of a variety of factors such as growing conditions, irrigation, fertilization, pruning, management and with climatic variation.

BRIEF DESCRIPTION OF THE DRAWING

The accompanying color photographic illustration shows typical specimens of the foliage and fruit of the present new grape variety 'Sugrafortyone'. The illustration shows the upper and lower surface of the leaves and exterior and sectional view of the fruit. The photographic illustration was taken shortly after the fruit was picked and the colors are as nearly true as is reasonably possible in a color representation of this type.

DETAILED DESCRIPTION OF THE PREFERRED EMBODIMENT

Throughout this specification, color names beginning with a small letter signify that the name of that color, as used in common speech, is aptly descriptive. Color names beginning with a capital letter designate values based upon The R.H.S. Colour Chart, published by The Royal Horticultural Society, London, England (2000).

Many of the description values in this specification are based on and conform to those set forth by the International Board for Plant Genetic Resources Institute Grape Descriptors (*Vitis* spp.) of 1983 and/or 1997, which was developed in collaboration with the Office International de la Vigne et du Vin (OIV) and the International Union for the Protection of New Varieties of Plants (UPOV).

The descriptive matter which follows pertains to 'Sugrafortyone' plants grown in the vicinity of Wasco, Kern County, Calif. during 2011, and is believed to apply to plants of the variety grown under similar conditions of soil and climate elsewhere.

VINE

General:

*Planting*.—Trained to a modified gable trellis, planted in about 7 ft.×12 ft. spacing.

*Practices*.—Gene-pool-vine: Cane pruned to approximately 36 spurs per vine. Test-vines: Cane pruned to approximately 36 spurs per vine.

*Size*.—Medium. Height: Approximately 2.0 m. Width: Approximately 2.2 m.

*Vigor*.—Vigorous.

*Fresh pruning weight*.—Approximately 7 kg per vine.

*Density of foliage*.—Dense.

*Productivity*.—Very productive — approximately 40 clusters per vine after thinning.

*Yield*.—Approximately 24 kg per vine.

*Crop load*.—Approximately 3.4 kg per vine (kg fruit per kg fresh-pruning-weight).

*Root stock*.—Not applicable.

*Own root*.—Yes.

*Resistance*.—Neither resistance nor susceptibility to diseases or pests has been observed in this variety.

Trunk:

*Shape*.—Circular.

*Diameter*.—Approximately 89 mm.

*Straps*.—Short.

*Surface texture*.—Shaggy.

*Inner bark color*.—Near Dark Grey Orange 165A.

*Outer bark color*.—Near Dark Greyed-green 197A and Near Medium Grey 201A.

SHOOTS

Young shoot:

*Form of tip*.—Half open.

*Distribution of anthocyanin coloration of tip*.—Striped.

*Intensity of anthocyanin coloration of tip*.—Weak.

*Density of prostrate hairs on tip*.—Medium.

*Density of erect hairs on tip*.—Absent.

Woody shoot (mature canes):

*Shape*.—Slender.

*Internode length*.—Approximately 62 mm.

*Width at node*.—Approximately 12 mm.

*Cross section*.—Circular.

*Surface*.—Smooth.

*Main color*.—Light brown, about Medium Greyed-Orange 164B to Near Light Greyed-Yellow 161A.

*Lenticels*.—Absent.

*Density of erect hairs on nodes*.—Absent or Very Sparse.

*Density of erect hairs on internodes*.—Absent or Very Sparse.

*Growth of auxiliary shoots*.—Medium; Average 19.5 cm/shoot.

Flowering shoot:

*Vigor during flowering*.—Strong.

*Attitude during flowering on shoots which are not tied*.—Semi-erect.

*Color of dorsal side of internodes*.—green with red highlights, about Medium Yellow-Green 144A and Dark Greyed-Purple 187A.

*Color of ventral side of internodes*.—green with red highlights, about Medium Yellow-Green 144A and Dark Greyed-Purple 187A.

*Color of dorsal side of nodes*.—green with red highlights, about Medium Yellow-Green 144A and Dark Greyed-Purple 187A.

*Color of ventral side of nodes*.—green with red highlights, about Medium Yellow-Green 144A and Dark Greyed-Purple 187A.

*Density of erect hairs on nodes*.—Absent.

*Erect hairs on internode*.—Absent.

*Density of prostrate hairs on nodes*.—Absent.

*Density of prostrate hairs on internodes*.—Absent.

*Anthocyanin coloration of buds*.—Absent.

Tendrils:

*Distribution on the shoot at full flowering*.—Discontinuous.

*Thickness*.—Medium.

*Color*.—Near Medium Yellow-Green 144C.

*Form*.—Bifurcated.

*Number of consecutive tendrils*.—Up to 2.

*Length of tendril*.—Long, approximately 19 cm.

LEAVES

Young Leaves:

*Color of upper surface of first 4 distal unfolded leaves*.—Near Yellow-Green 145A.

*Average intensity of anthocyanin coloration of six distal leaves prior to flowering*.—Absent.

*Density of prostrate hairs between veins at lower surface of 4th distal unfolded leaf*.—Absent.

*Density of erect hairs between veins at lower surface of 4th distal unfolded leaf*.—Absent.

*Density of prostrate hairs on veins at lower surface of 4th distal unfolded leaf*.—Absent.

*Density of erect hairs on veins at lower surface of 4th distal unfolded leaf*.—Absent.

Mature leaves:

*Average length*.—Approximately 143 mm from ending of petiole to tip of leaf.

*Average width*.—Approximately 190 mm.

*Size of blade*.—Medium.

*Shape of blade*.—Pentagonal.

*Number of lobes*.—Approximately 5.

*Anthocyanin coloration of main veins on the upper side of the blade*.—Absent.

*Mature leaf profile*.—Flat.

*Blistering surface of blade upper surface*.—Absent.

*Leaf blade tip*.—In the plane of the leaf.

*Undulation of margin*.—Slight.

*Thickness*.—Medium.

*Undulation of blade between main and lateral veins*.—Absent.

*Shape of teeth*.—Both sides rectilinear in most cases with some convex shaped.

*Length of teeth*.—Medium, usually 5 to 15 mm, average 10 mm.
*Ratio length/width of teeth*.—Small.
*General shape of petiole sinus*.—Slightly open.
*Tooth at petiole sinus*.—Absent.
*Petiole sinus limited by veins*.—Absent.
*Shape of upper lateral sinus*.—Open.
*Depth of upper lateral sinus*.—Very Shallow.
*Density of prostrate hairs between veins on lower surface of blade*.—Absent.
*Density of erect hairs between veins on lower surface of blade*.—Absent.
*Density of prostrate hairs on main veins on lower surface of blade*.—Absent.
*Density of erect hairs on main veins on lower surface of blade*.—Absent.
*Density of prostrate hairs on main veins on upper surface of blade*.—Absent.
*Autumn coloration of leaves*.—Dark Green, about 135A, to Medium Yellow, about 11B, to Reddish-Brown, about 178C, in late November.

Upper surface:
*Color*.—Near Dark Green 135A.
*Surface texture*.—Smooth.
*Surface appearance*.—Semi-Glossy to Dull.
*Glossiness*.—Weak.
*Pubescence*.—Absent.

Lower surface:
*Color*.—Near Medium Green 135C.
*Anthocyanin coloration of main veins on lower leaf surface*.—Absent.
*Glossiness*.—Weak.
*Pubescence*.—Absent.
*Surface texture*.—Smooth.
*Surface appearance*.—Dull.

Petiole:
*Length of petiole*.—Medium, Approximately 10 cm.
*Length of petiole compared to middle vein*.—Much shorter.
*Diameter*.—Approximately 4 mm.
*Density of prostrate hairs on petiole*.—Absent.
*Density of erect hairs on petiole*.—Absent.
*Shape of base of petiole sinus*.—U-shaped.
*Color*.—Light Green 142A to Light Green 142C with highlights of Medium Greyed-Red 182B.

Buds:
*Shape*.—Conical.
*Size*.—Medium, approximately 3 mm×4 mm.
*Position*.—Slightly held out.
*Cane bud fruitfulness*.—Basal most fruitful, $3^{rd}$ to $5^{th}$ bud position.
*Time of bud burst*.—Early, about March 8th.

FLOWERS

General:
*Flower sex*.—Hermaphrodite.
*Length of first inflorescence*.—Medium, about 18 cm.
*Position of first flowering node*.—Fifth node.
*Number of inflorescences per shoot*.—Approximately 1 to 2.
*Date of full bloom*.—Approximately May 5th.
*Size (diameter of fully open flower)*.—Medium, approximately 6 mm.

FRUIT

General:
*Ripening period*.—Early, approximately July 3-14.
*Use*.—Table grape fresh consumption.
*Keeping quality*.—Good.
*Shipping quality*.—Good.
*Date of first harvest*.—Approximately July 3rd.
*Solids-sugar*.—Medium.
*Refractometer test*.—Approximately 17%.
*Acid*.—Medium, approximately 0.55 gr./L tartaric acid.
*Juice pH*.—Approximately 3.4.
*Tendency to crack*.—Low.
*Sensitivity to sunburn*.—Absent.
*Fruit shrivel after ripe*.—Only when drying to raisins.
*Secondary cluster*.—Occasional.
*Resistance*.—Absent.

Cluster:
*Bunch size (peduncle excluded)*.—Medium.
*Bunch length (peduncle excluded)*.—Medium, approximately 19 cm.
*Bunch width*.—Approximately 16 cm.
*Bunch weight*.—Medium, approximately 450 g.
*Bunch density*.—Medium.
*Number of berries*.—Approximately 85.
*Form*.—Conical-shaped.

Peduncle:
*Length of peduncle*.—Medium, approximately 40 mm.
*Lignification of peduncle*.—Medium.
*Color*.—Near Medium Green 141C.

Berry:
*Size*.—Medium.
*Uniformity of size*.—Slightly variable.
*Berry weight*.—Medium, approximately 5.1 gr. treated.
*Gibberellic acid treated*.—High, 20 ppm for sizing
*Shape*.—Somewhat round.
*Presence of seeds*.—Rudimentary.
*Cross section*.—Round.
*Dimensions*.—Longitudinal axis: Approximately 21 mm treated. Horizontal axis: Approximately 20 mm treated.
*Skin color (without bloom)*.—Near Medium Yellow-Green 149A, becoming more yellow as it ripens to near Light Yellow-Green 154A.
*Flesh color*.—Near Light Yellow-Green 154D.
*Juiciness of flesh*.—Slightly juicy.
*Berry firmness*.—Firm.
*Particular flavor*.—Muscat.
*Bloom (cuticular wax)*.—Medium.
*Pedicel length*.—Medium, approximately 7.0 mm.
*Berry separation from pedicel*.—Medium.
*Visibility of hilum*.—Visible.

Skin:
*Thickness*.—Medium.
*Texture*.—Smooth.
*Reticulation*.—Absent.
*Roughness*.—Absent.
*Tenacity*.—Tenacious to flesh.

Seed:
*Number of seeds per berry*.—Usually 1, sometimes 2.
*Size*.—Small.
*Color*.—Near Light Yellow-Green 154C.

*Texture*.—Medium.
*Endosperm*.—Slight.
*Fresh weight of seed-traces/berry*.—Approximately 2.47 mg.
*Room-dry weight of seed-traces/berry*.—Approximately 1.55 mg.

What is claimed is:

1. A new and distinct variety of grapevine as herein illustrated and described.

* * * * *

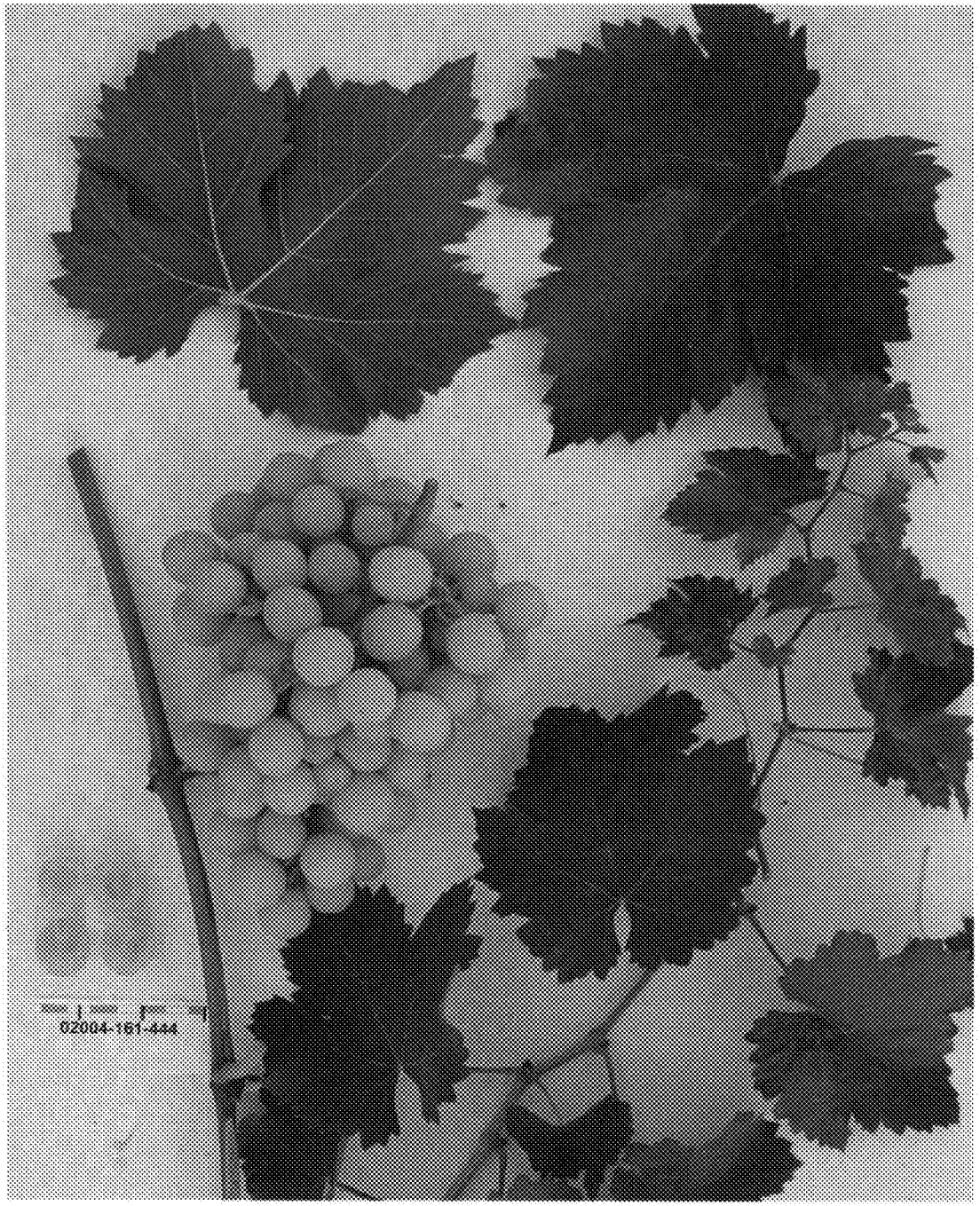
02004-161-444